United States Patent
Sapida et al.

(10) Patent No.: US 8,262,609 B2
(45) Date of Patent: Sep. 11, 2012

(54) ANTERIOR INFLATION BALLOON

(75) Inventors: Warren C. Sapida, Santa Clara, CA (US); Bryan J. Auyoung, Santa Clara, CA (US); Hester Chan, Sunnyvale, CA (US); Todd W. Jenkins, San Jose, CA (US)

(73) Assignee: Kyphon Sarl, Neuchatel (CH)

(*) Notice: Subject to any disclaimer, the term of this patent is extended or adjusted under 35 U.S.C. 154(b) by 397 days.

(21) Appl. No.: 12/608,935

(22) Filed: Oct. 29, 2009

(65) Prior Publication Data
US 2011/0106184 A1 May 5, 2011

(51) Int. Cl.
*A61M 29/00* (2006.01)
(52) U.S. Cl. .................. 604/96.01; 604/103.01
(58) Field of Classification Search .......... 604/95.03, 604/95.04, 96.01, 103.07, 915, 103.04, 103.08, 604/105
See application file for complete search history.

(56) References Cited

U.S. PATENT DOCUMENTS

| | | | |
|---|---|---|---|
| 4,969,888 A | 11/1990 | Scholten et al. | |
| 5,250,029 A | 10/1993 | Lin et al. | |
| 5,843,116 A * | 12/1998 | Crocker et al. | 606/192 |
| 5,972,015 A | 10/1999 | Scribner et al. | |
| 6,129,737 A | 10/2000 | Hamilton et al. | |
| 6,248,110 B1 | 6/2001 | Reiley et al. | |
| 6,352,551 B1 * | 3/2002 | Wang | 623/1.11 |
| 6,544,224 B1 * | 4/2003 | Steese-Bradley | 604/103.06 |
| 6,558,390 B2 | 5/2003 | Cragg | |
| 6,719,773 B1 | 4/2004 | Boucher | |
| 7,241,303 B2 | 7/2007 | Reiss et al. | |
| 2006/0100706 A1 | 5/2006 | Shadduck et al. | |
| 2009/0254064 A1 * | 10/2009 | Boatman | 604/509 |

FOREIGN PATENT DOCUMENTS

| | | |
|---|---|---|
| WO | 2008026888 A1 | 3/2008 |
| WO | 2009036466 A1 | 11/2011 |

OTHER PUBLICATIONS

Form PCT/ISA/219, International Search Report for International Application No. PCT/US2010/050357.

* cited by examiner

*Primary Examiner* — Quynh-Nhu H Vu

(57) ABSTRACT

An inflatable bone tamp for performing a minimally invasive surgical procedure includes an inflatable structure that exhibits an outwardly tapering expansion profile. The outward taper can beneficially allow the inflatable bone tamp to exert greater targeted force in difficult environments. For example, in a vertebra with a compression fracture, the outwardly tapering expansion profile of the inflatable bone tamp can result in greater lifting force being applied to the endplates of the vertebra, thereby increasing the likelihood of restoring the height lost due to the compression fracture.

8 Claims, 16 Drawing Sheets

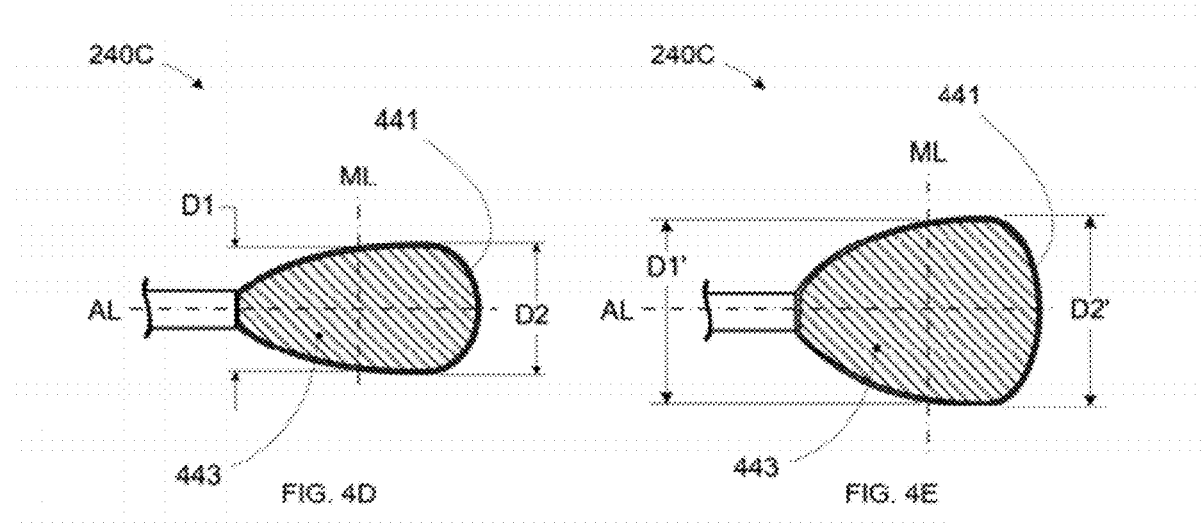
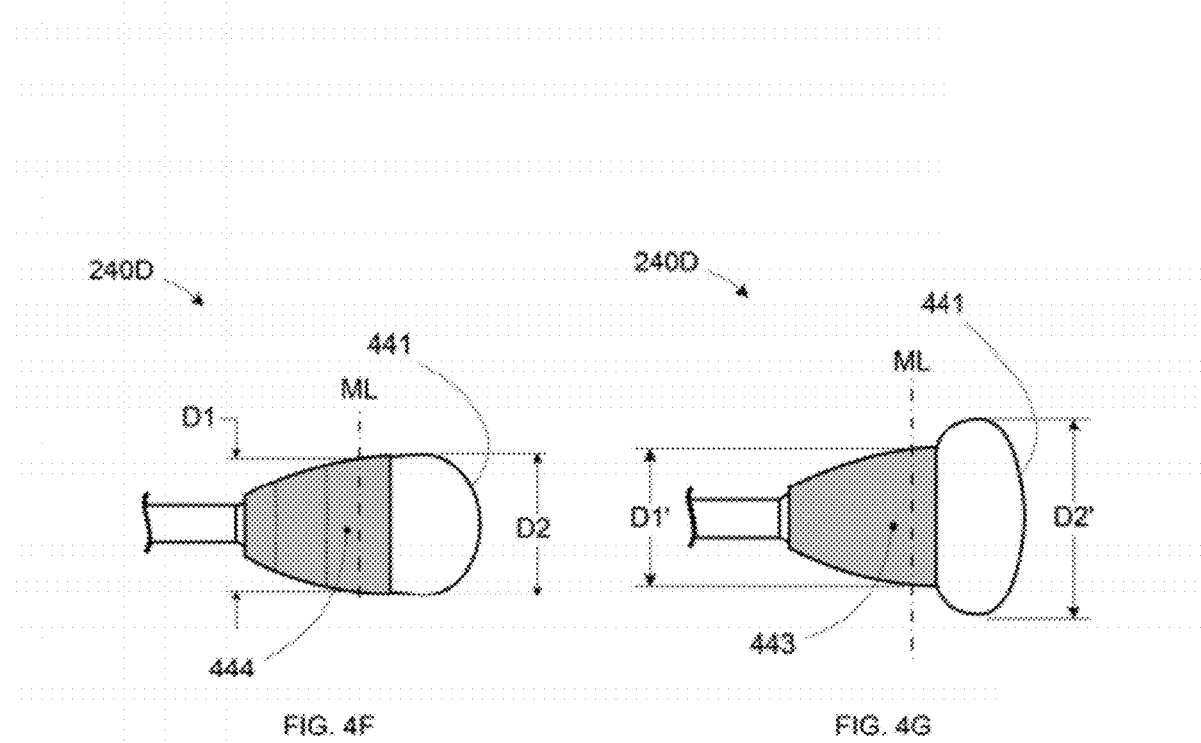

ANTERIOR INFLATION BALLOON

FIELD OF THE INVENTION

The invention relates to a system and method for performing a surgical procedure, and in particular, to an inflatable device that exhibits greater distal than proximal expansion to manipulate bone.

BACKGROUND OF THE INVENTION

A minimally invasive procedure is a medical procedure that is performed through the skin or an anatomical opening. In contrast to an open procedure for the same purpose, a minimally invasive procedure will generally be less traumatic to the patient and result in a reduced recovery period.

However, there are numerous challenges that minimally invasive procedures present. For example, minimally invasive procedures are typically more time-consuming than their open procedure analogues due to the challenges of working within a constrained operative pathway. In addition, without direct visual feedback into the operative location, accurately selecting, sizing, placing, and/or applying minimally invasive surgical instruments and/or treatment materials/devices can be difficult.

For example, for many individuals in our aging world population, undiagnosed and/or untreatable bone strength losses have weakened these individuals' bones to a point that even normal daily activities pose a significant threat of fracture. In one common scenario, when the bones of the spine are sufficiently weakened, the compressive forces in the spine can cause fracture and/or deformation of the vertebral bodies. For sufficiently weakened bone, even normal daily activities like walking down steps or carrying groceries can cause a collapse of one or more spinal bones. A fracture of the vertebral body in this manner is typically referred to as a vertebral compression fracture. Other commonly occurring fractures resulting from weakened bones can include hip, wrist, knee and ankle fractures, to name a few.

Fractures such as vertebral compression fractures often result in episodes of pain that are chronic and intense. Aside from the pain caused by the fracture itself, the involvement of the spinal column can result in pinched and/or damaged nerves, causing paralysis, loss of function, and intense pain which radiates throughout the patient's body. Even where nerves are not affected, however, the intense pain associated with all types of fractures is debilitating, resulting in a great deal of stress, impaired mobility and other long-term consequences. For example, progressive spinal fractures can, over time, cause serious deformation of the spine ("kyphosis"), giving an individual a hunched-back appearance, and can also result in significantly reduced lung capacity and increased mortality.

Because patients with these problems are typically older, and often suffer from various other significant health complications, many of these individuals are unable to tolerate invasive surgery. Therefore, in an effort to more effectively and directly treat vertebral compression fractures, minimally invasive techniques such as vertebroplasty and, subsequently, kyphoplasty, have been developed. Vertebroplasty involves the injection of a flowable reinforcing material, usually polymethylmethacrylate (PMMA—commonly known as bone cement), into a fractured, weakened, or diseased vertebral body. Shortly after injection, the liquid filling material hardens or polymerizes, desirably supporting the vertebral body internally, alleviating pain and preventing further collapse of the injected vertebral body.

Because the liquid bone cement naturally follows the path of least resistance within bone, and because the small-diameter needles used to deliver bone cement in vertebroplasty procedure require either high delivery pressures and/or less viscous bone cements, ensuring that the bone cement remains within the already compromised vertebral body is a significant concern in vertebroplasty procedures. Kyphoplasty addresses this issue by first creating a cavity within the vertebral body (e.g., with an inflatable balloon) and then filling that cavity with bone filler material. The cavity provides a natural containment region that minimizes the risk of bone filler material escape from the vertebral body. An additional benefit of kyphoplasty is that the creation of the cavity can also restore the original height of the vertebral body, further enhancing the benefit of the procedure.

Conventional inflatable bone tamps (IBTs) used in kyphoplasty procedures incorporate balloons that exhibit generally symmetrical free expansion profiles about the midlines of the balloons. In other words, the proximal and distal halves of the balloon expand at substantially the same rates and to substantially the same sizes as inflation fluid is delivered to the balloon. Note that "free expansion" refers to expansion in free space, rather than within the target environment, such as within a vertebral body.

In general, a balloon exhibiting symmetrical free expansion will expand along a path of least resistance when inflated within its target environment, which can result in less than optimal procedure results. For example, FIGS. 1A-1C depict the use of a conventional IBT 130 to prepare a fractured vertebra 102 to be filled with bone cement (as part of a kyphoplasty procedure). Due to a compression fracture in vertebral body 102, the spinal column portion represented by vertebral bodies 101, 102, and 103 exhibit an abnormal spinal curvature (kyphosis) CK that can lead to severe pain and further fracturing of adjacent vertebral bodies if left untreated.

As shown in FIG. 1A, kyphoplasty is a performed by creating an access path to the target vertebral body (102) using a cannula 104. An inflatable bone tamp 130 is placed into an interior lumen 104-L of cannula 104. Inflatable bone tamp 130 includes a catheter 132, a balloon 140 at the distal end of catheter 132, and a connector 131 (e.g., a Luer Lock fitting) at the proximal end of catheter 132. Balloon 140 is a conventional kyphoplasty balloon that exhibits a symmetrical free expansion profile.

Inflatable bone tamp 130 is coupled to an inflation syringe 110 by flexible tubing 120. Syringe 110 includes a barrel 111 and a plunger 113 that is slidably disposed in barrel 111. To inflate balloon 140, a force is applied to plunger 113 to express inflation fluid 115 through tubing 120, connector 131, and catheter 132, and into balloon 140. This delivery of inflation fluid 115 cause inflatable structure to begin to expand, as shown in FIG. 1B. As balloon 140 expands, it compresses the surrounding cancellous bone 102-C to create a cavity within fractured vertebra 102. Ideally, balloon 140 would also force endplates 102-E of vertebra 102 apart to restore the vertebral body height lost due to the compression fracture.

However, in many instances, a fractured vertebra "sets" in its fractured condition, as the bone partially heals in its compressed state. Therefore, because, balloon 140 will exhibit expansion along the path of least resistance within vertebral body 102, in such cases balloon 140 will expand towards the posterior of vertebra 102, continuing to compress cancellous bone 102-C rather than forcing apart endplates 102-E, as shown in FIG. 1C. In essence, due to the symmetrical expansion properties of balloon 140, the hard endplates 102-E act as a channel that guides expansion of balloon 140 into the softer cancellous bone 102-C, where the inflation force acts to compress the cancellous bone 102-C, rather than restore the height of vertebra 102. Consequently, the kyphosis (curvature CK) caused by the fracture of vertebra 102 is not corrected.

Accordingly, it is desirable to provide surgical tools and techniques that provide more effective vertebral body height restoration during the treatment of compression fractures.

SUMMARY OF THE INVENTION

By providing a bone tamp with an inflatable structure having an expansion profile that exhibits greater distal expansion than proximal expansion (i.e., outwardly tapering), a kyphoplasty procedure can be performed in which lifting forces are more effectively applied to the endplates of a collapsed vertebral body, thereby enhancing the likelihood of height restoration of the vertebral body during the procedure.

As used herein, "expansion profile" refers to the shape of an inflatable structure during elastic expansion of the structure (i.e., expansion beyond the inflated, non-distended state of the structure). Furthermore, "outwardly tapering" refers to a state in which a maximum dimension (e.g., radial diameter, radial width or height) of a proximal half of the inflatable structure is less than a maximum dimension of a distal half of the inflatable structure.

In one embodiment, an inflatable bone tamp can include an inflatable structure formed from multiple curved lobes, such as a proximal lobe and a distal lobe. By sizing the distal lobe(s) to have a larger maximum non-distended radial diameter larger than a maximum non-distended radial diameter of the proximal lobe(s), the inflatable structure will exhibit an outwardly tapering profile when inflated.

In various other embodiments, an outwardly tapering inflation profile can be incorporated into an inflatable structure via features on the surface of an inflatable element (e.g., regions of additional material such as strips or bands), features within an inflatable element (e.g., internal webbing or straps), wall thickness variations in an inflatable element, or even external restraints that fit over an inflatable element (e.g., stents, sleeves, or strings).

In another embodiment, a surgical system for treating bone can include one or more inflatable bone tamps exhibiting outwardly tapering inflation profiles. The surgical system can further include additional equipment for performing a surgical procedure (e.g., one or more cannulas sized to accept the inflatable bone tamps, access tools such as drills, guide wires, obturators, trocars, and/or curettes) and/or instructions for performing the surgical procedure using the one or more inflatable bone tamps.

In various other embodiments, a surgical procedure such as kyphoplasty can be performed by creating an access path using a cannula, inserting an inflatable bone tamp having an outwardly tapering inflation profile into a target bone (e.g., a fractured vertebra) via the cannula, inflating the bone tamp to create a cavity in cancellous bone and restore the original cortical bone profile (e.g., restore vertebral body height), deflating and removing the inflatable bone tamp, and then filling the cavity with bone filler material to support the treated bone.

In a procedure such as kyphoplasty, the outwardly tapering expansion profile of the inflatable bone tamp allows the inflation force of the bone tamp to be more effectively directed towards the endplates of the fractured vertebra. This in turn enhances the ability of the bone tamp to restore the height of the vertebra, rather than simply compacting a larger portion of cancellous bone within the vertebra.

As will be realized by those of skilled in the art, many different embodiments of an inflatable bone tamp exhibiting an outwardly tapering expansion profile, systems, kits, and/or methods of using such an inflatable bone tamp according to the present invention are possible. Additional uses, advantages, and features of the invention are set forth in the illustrative embodiments discussed in the detailed description herein and will become more apparent to those skilled in the art upon examination of the following.

BRIEF DESCRIPTION OF THE DRAWINGS

FIGS. 4A-4G show alternative embodiments for outwardly tapering inflation structures for an inflatable bone tamp.

DETAILED DESCRIPTION

By providing a bone tamp with an inflatable structure having an expansion profile that exhibits greater distal expansion than proximal expansion (i.e., outwardly tapering), a kyphoplasty procedure can be performed in which lifting forces are more effectively applied to the endplates of a collapsed vertebral body, thereby enhancing the likelihood of height restoration of the vertebral body during the procedure.

Figure 2A:
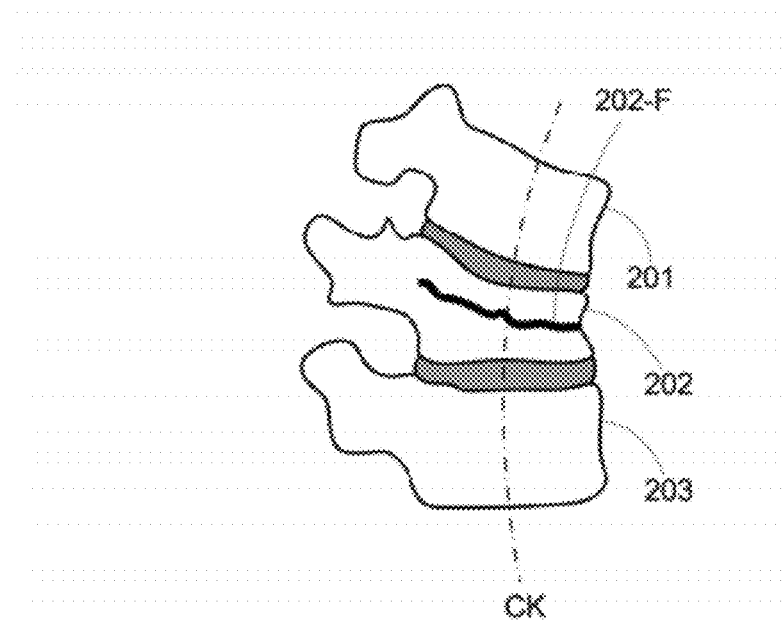
FIGS. 2A-2H show an exemplary kyphoplasty procedure that incorporates an inflatable bone tamp exhibiting an outwardly tapering inflation profile.

FIGS. 2A-2H show an exemplary kyphoplasty procedure using an inflatable bone tamp exhibiting an outwardly tapering inflation profile. FIG. 2A shows a portion of a human vertebral column having vertebrae 201, 202, and 203. Vertebra 202 has collapsed due to a vertebral compression fracture (VCF) 202-F that could be the result of osteoporosis, cancer-related weakening of the bone, and/or physical trauma. The abnormal curvature CK of the spine caused by VCF 202-F can lead to severe pain and further fracturing of adjacent vertebral bodies.

Figure 2B:
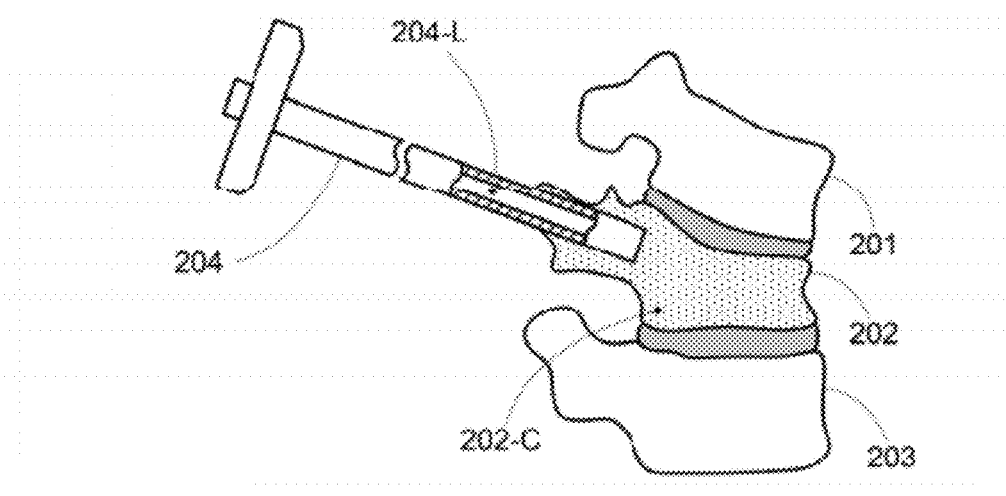

FIG. 2B shows a cannula 204 being positioned next to the target surgical location, which in this case is the cancellous bone structure 202-C within fractured vertebra 202. In this manner, a percutaneous path to vertebra 202 is provided via an interior lumen 204-L of cannula 204. Typically, cannula 204 is docked into the exterior wall of the vertebral body (using either a transpedicular or extrapedicular approach) using a guide needle and/or dissector, after which a drill or other access tool (not shown) is used to create a path further into the cancellous bone 202-C of vertebra 202. However, any other method of cannula placement can be used to position cannula 204.

Figure 2C:
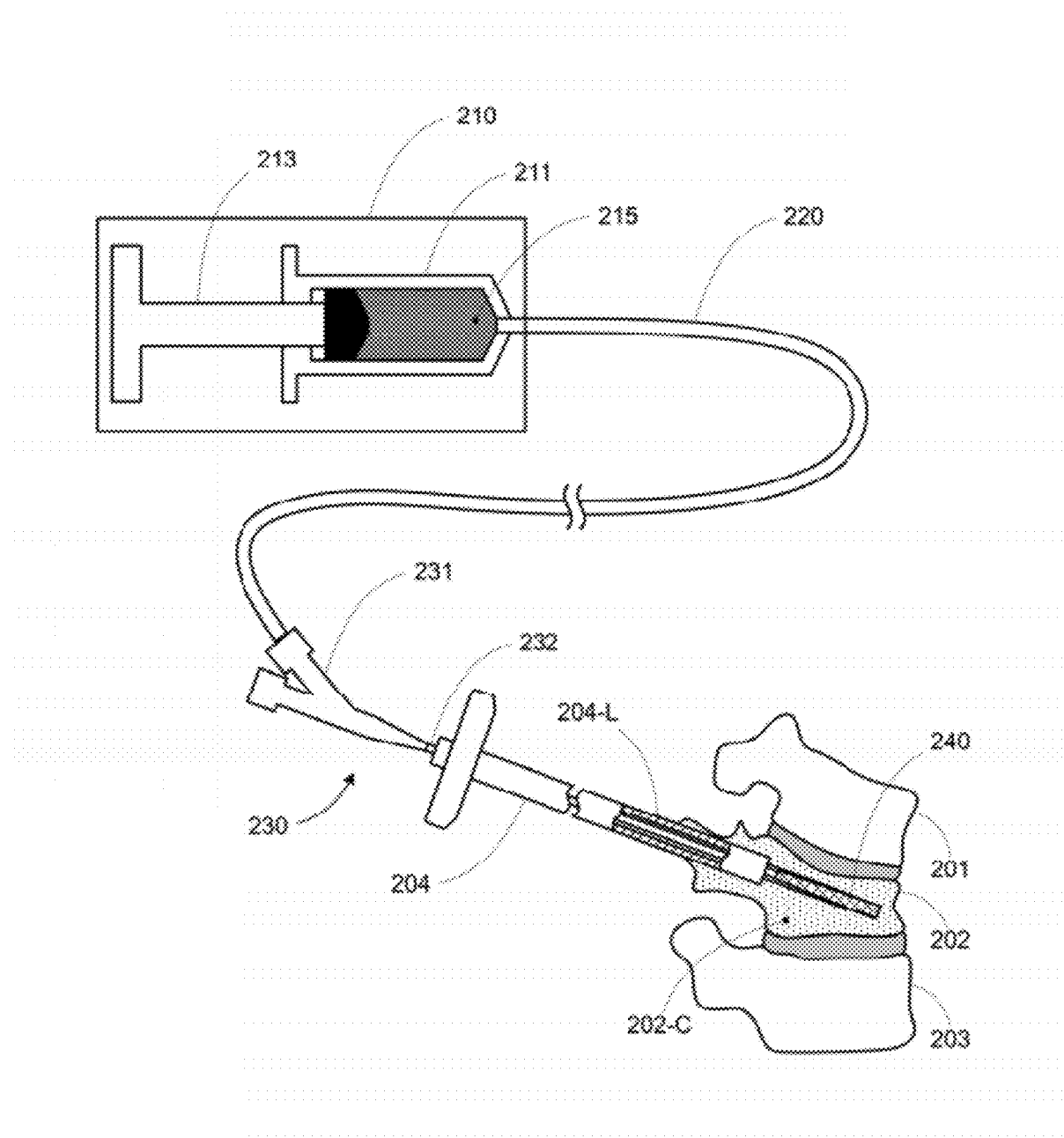

Then in FIG. 2C, an inflatable bone tamp 230 is placed into cannula 204. Inflatable bone tamp 230 includes a shaft 232 (e.g., a catheter), an inflatable structure 240 (e.g., a balloon) at the distal end of shaft 232, and a connector 231 (e.g., a Luer Lock fitting) at the proximal end of shaft 232. Inflatable bone tamp 230 is coupled to inflation mechanism 210 by a flow channel 220 (e.g., flexible tubing). For exemplary purposes, inflation mechanism 210 is depicted as a syringe having a plunger 213 for expressing inflation fluid 215 (e.g., saline solution, air, contrast solution, or any other fluid) from a barrel 211. Note that in various other embodiments, inflation mechanism 210 can be any system for delivering inflation, such as a syringe, pump, or compressed gas system, among others. Furthermore, in various other embodiments, inflation mechanism 210 can be directly connected to inflatable bone tamp 231.

Inflatable structure 240 is configured to exhibit an outwardly tapering inflation profile (i.e., greater distal expansion than proximal expansion during elastic free expansion). In other words, once inflatable structure 240 is inflated to a working level (i.e., is inflated beyond its inflated, non-distended shape), the maximum distal dimension of inflatable structure 240 is greater than its maximum proximal dimension. This behavior is described in greater detail below with respect to FIGS. 3A-3E and 4A-4G. Due to this outwardly tapering expansion characteristic of inflatable structure 240, inflatable bone tamp 230 is particularly well-suited to manipulate typical vertebral compression fractures.

Figure 2D:
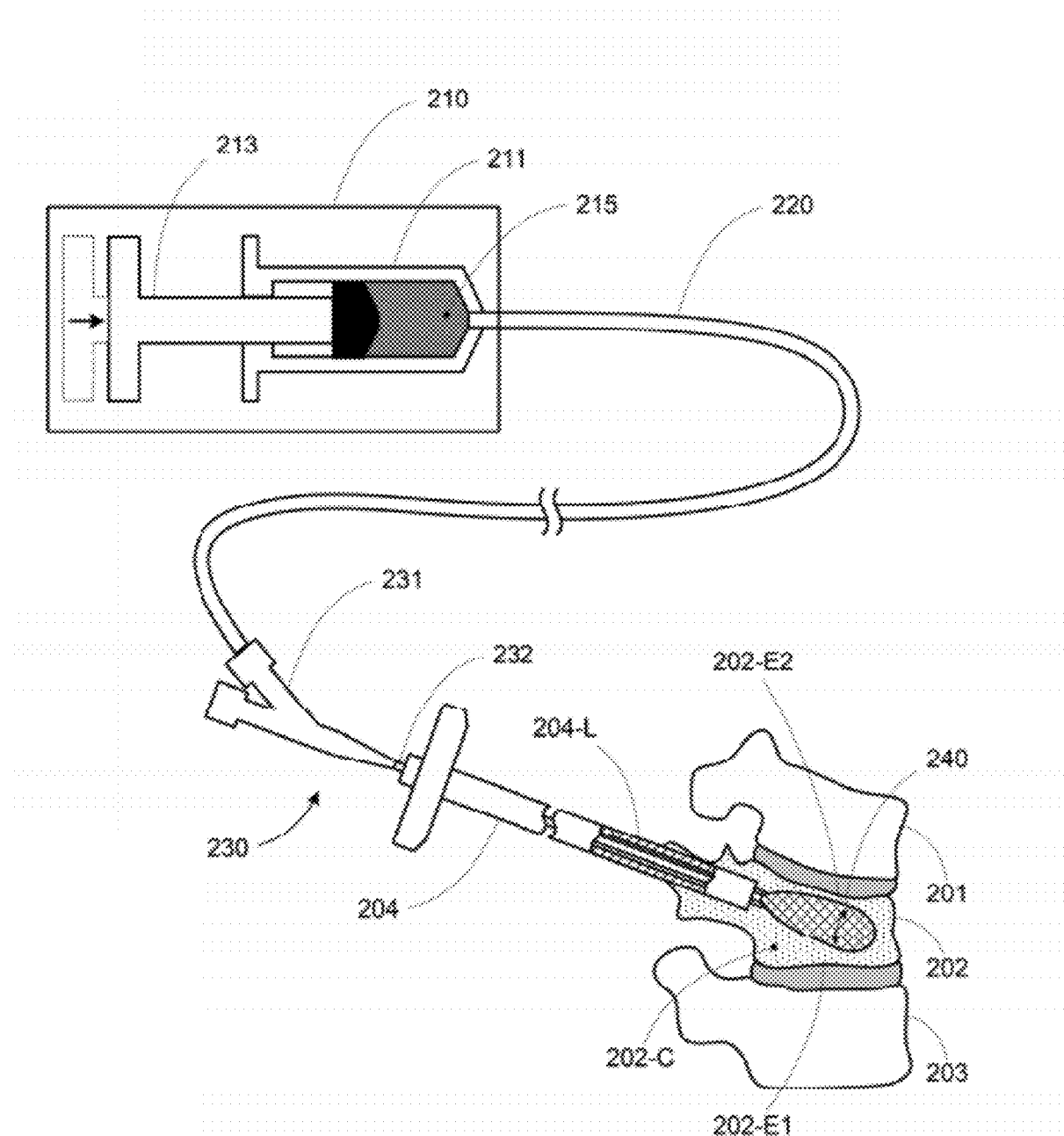

Specifically, as shown in FIG. 2D, as inflation mechanism 210 is actuated to drive inflation fluid 215 into inflatable structure 240, inflatable structure 240 begins to expand within fractured vertebra 202. For example, in the embodiment shown in FIG. 2D, a force is applied to drive plunger 213 through barrel 211, thereby expressing inflation fluid 215 through flow channel 220, connector 231, shaft 232, and into inflatable structure 240. The resulting expansion of inflatable structure 240 initially compresses the surrounding cancellous bone 202-C to begin creating a cavity within vertebra 202.

Figure 1A:
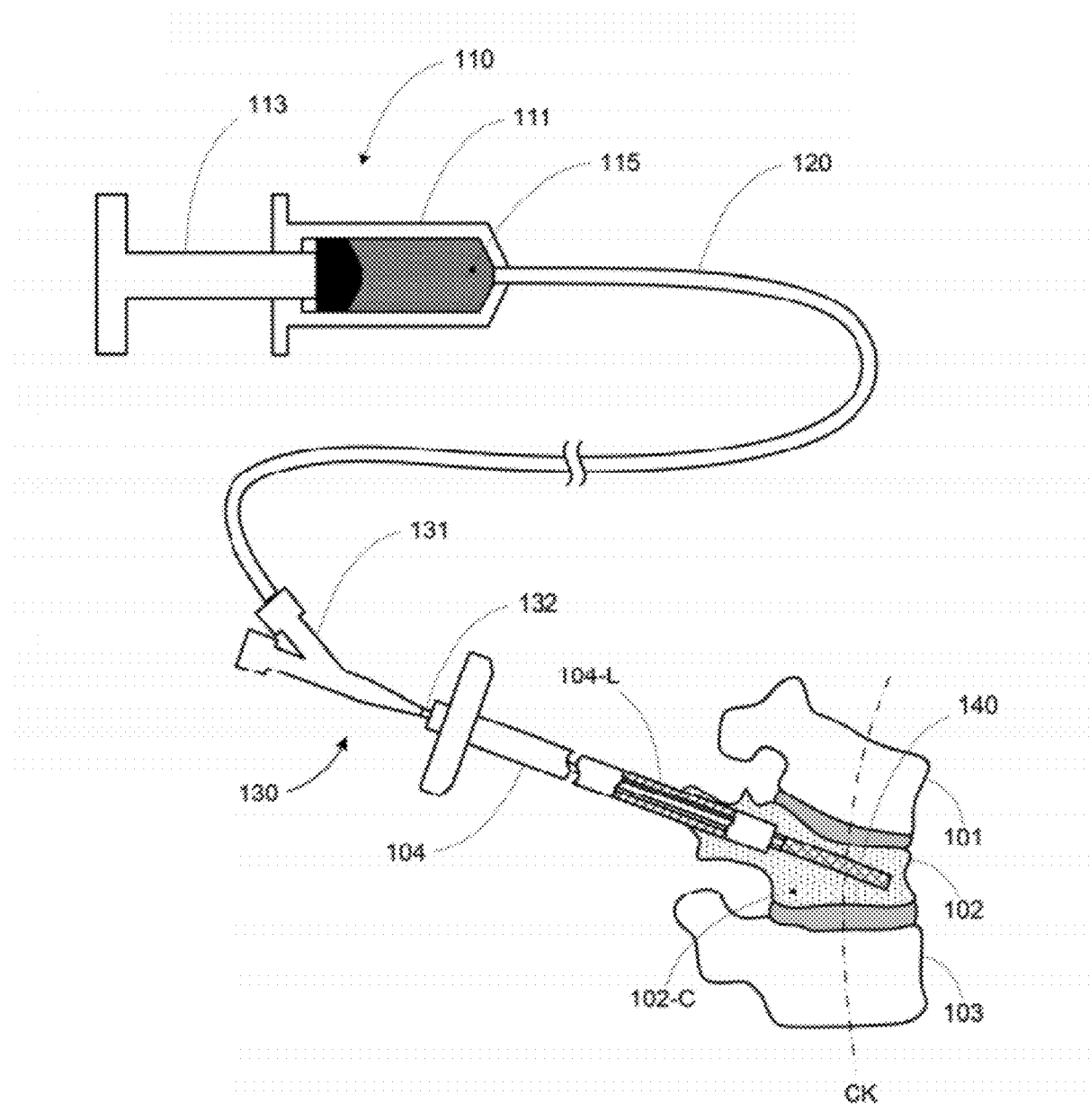
FIGS. 1A-1C show the use of a conventional inflatable bone tamp in a vertebra that has undergone a compression fracture and has at least partially set in its compressed state.
Figure 1B:
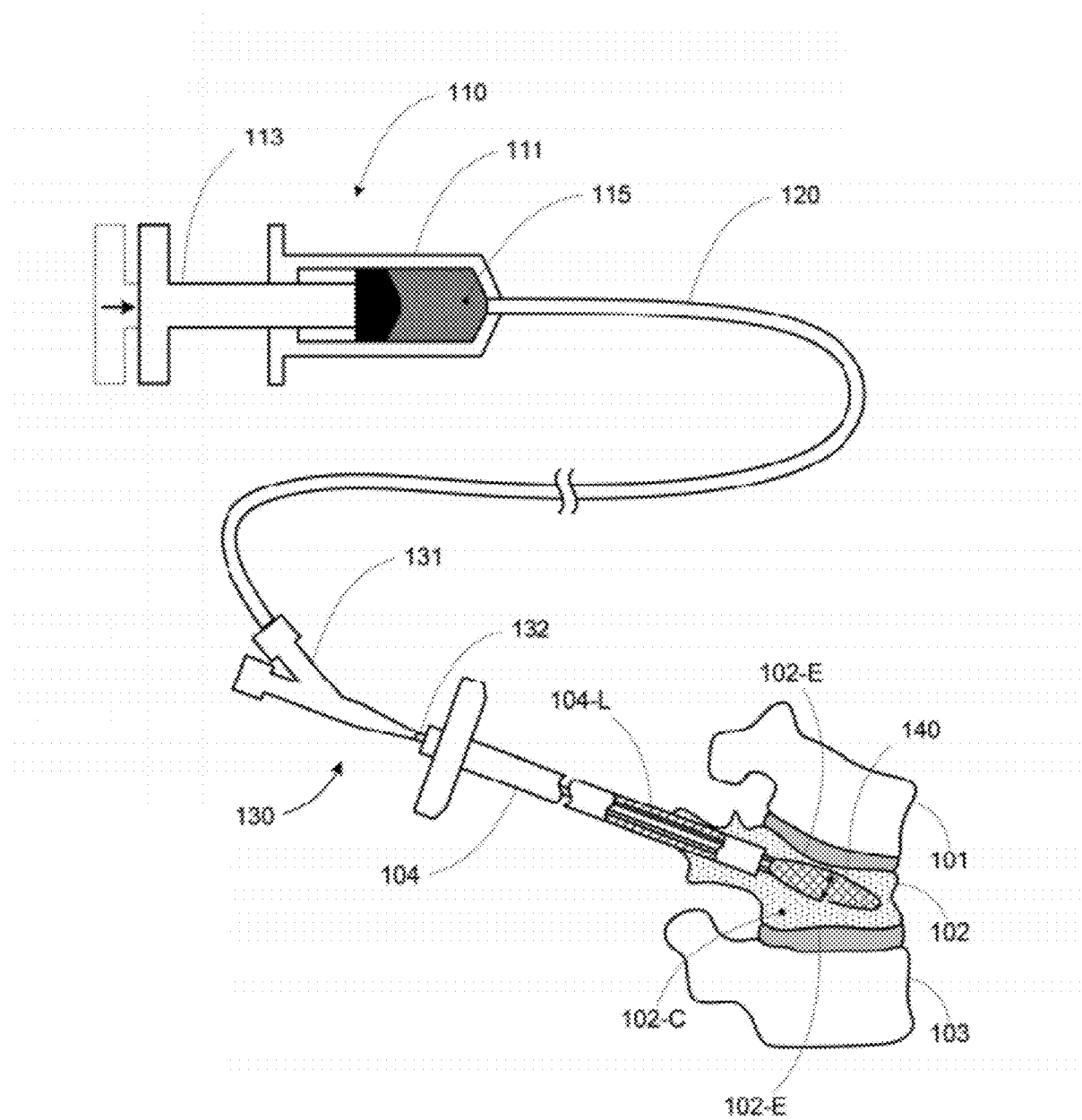
Figure 1C:
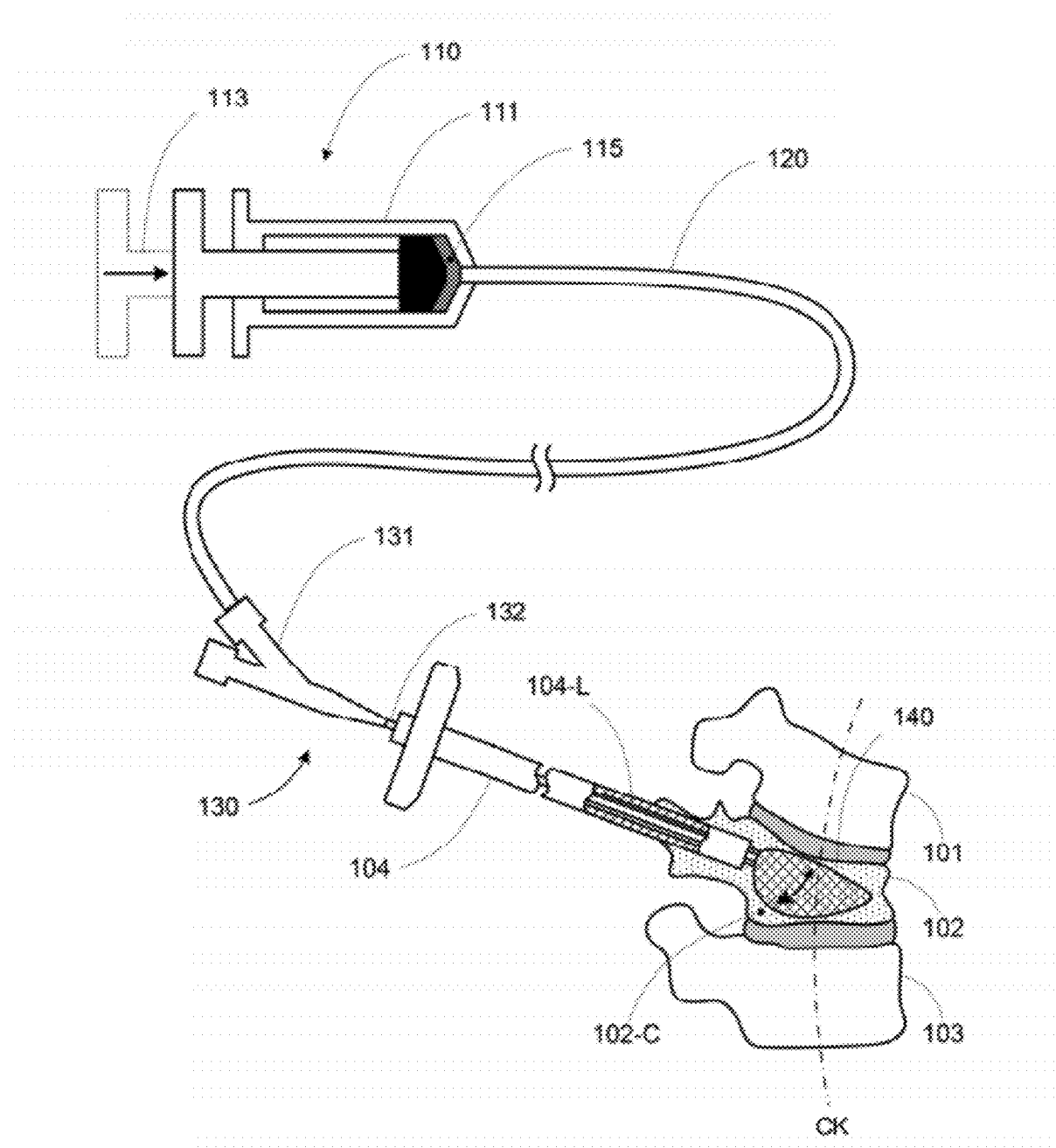
Figure 2E:
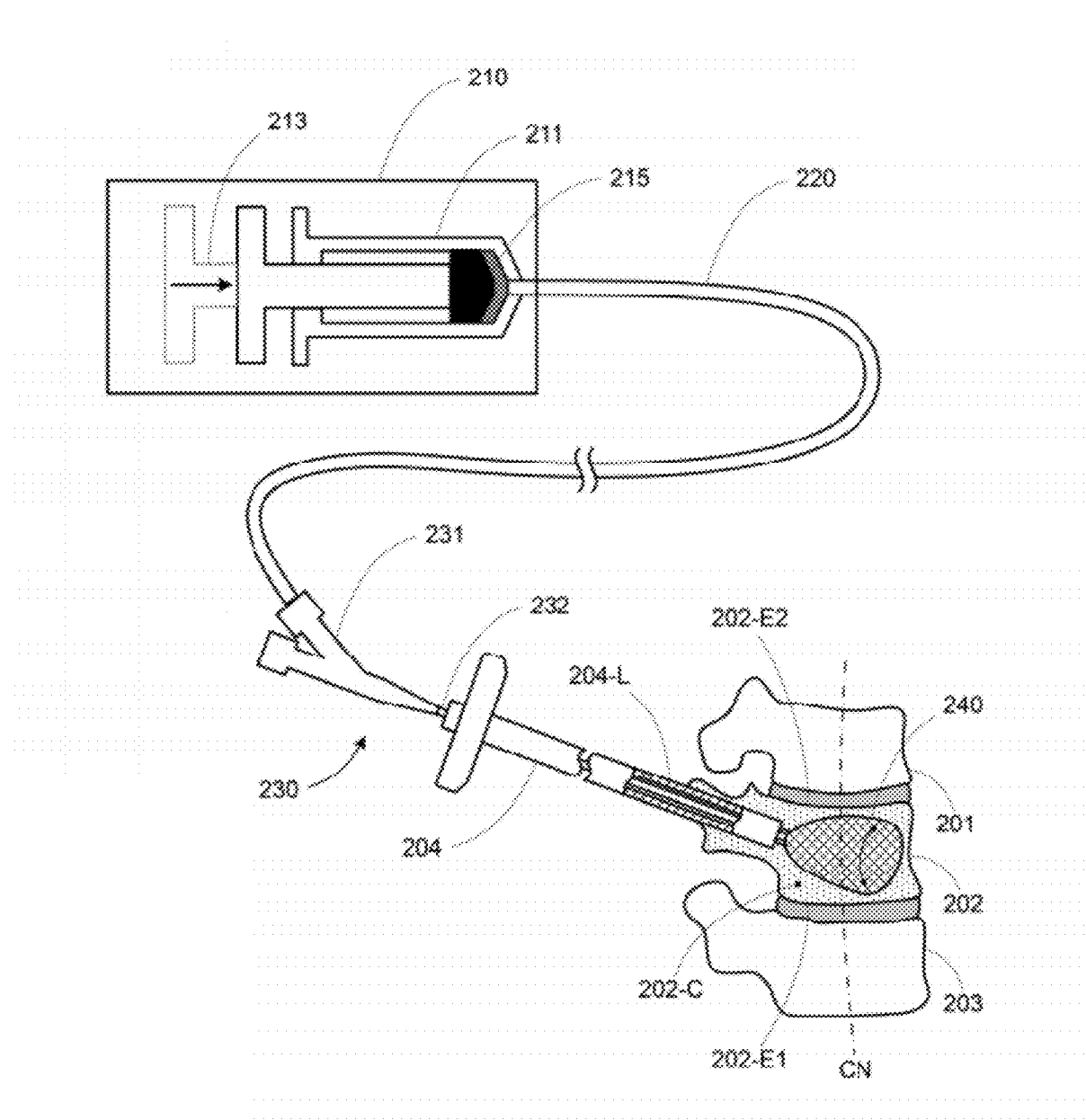

As inflatable structure 240 continues to compress cancellous bone 202-C as it expands, it approaches the harder endplates 202-E1 (inferior) and 202-E2 (superior) of vertebra 202. However, unlike conventional (symmetrically expanding) inflatable bone tamps, as described with respect to FIGS. 1A-1C, inflatable structure 240 does not expand into the posterior region of vertebra 202 in response to the resistance provided by endplates 202-E1 and 202-E2. Instead, the outwardly tapering characteristic of inflatable structure 240 tends to bias the expansion of inflatable structure 240 towards the anterior of vertebra 202, as shown in FIG. 2E. This anterior inflation results in a greater force being applied to move endplates 202-E1 and 202-E2 apart, thereby increasing the likelihood of successful height restoration of fractured vertebra 202.

Figure 2F:
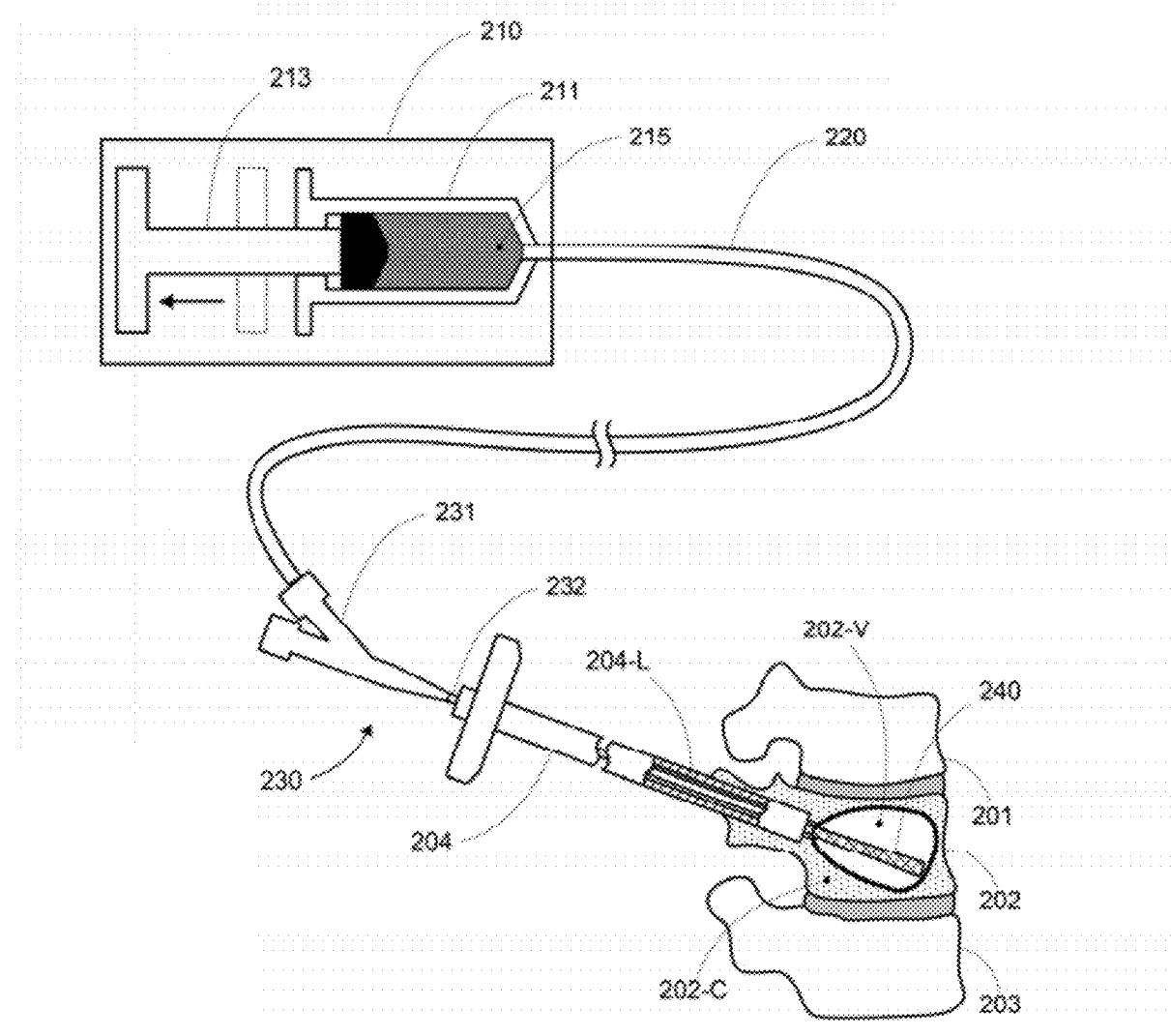

Once inflatable structure 240 has been expanded to a desired volume and/or a desired height restoration has been achieved in vertebra 202, inflatable structure 240 is deflated, as shown in FIG. 2F. Note that in some embodiments, the outwardly tapering characteristic of inflatable structure 240 is derived from a physical construction that also enhances the removability of inflatable bone tamp 230 from cannula 204. Specifically, a generally smaller proximal section of inflatable structure 240 can make inflatable structure 240 easier to draw into lumen 204-L of cannula 204 as inflatable bone tamp 230 is being withdrawn from vertebra 202.

Figure 2G:
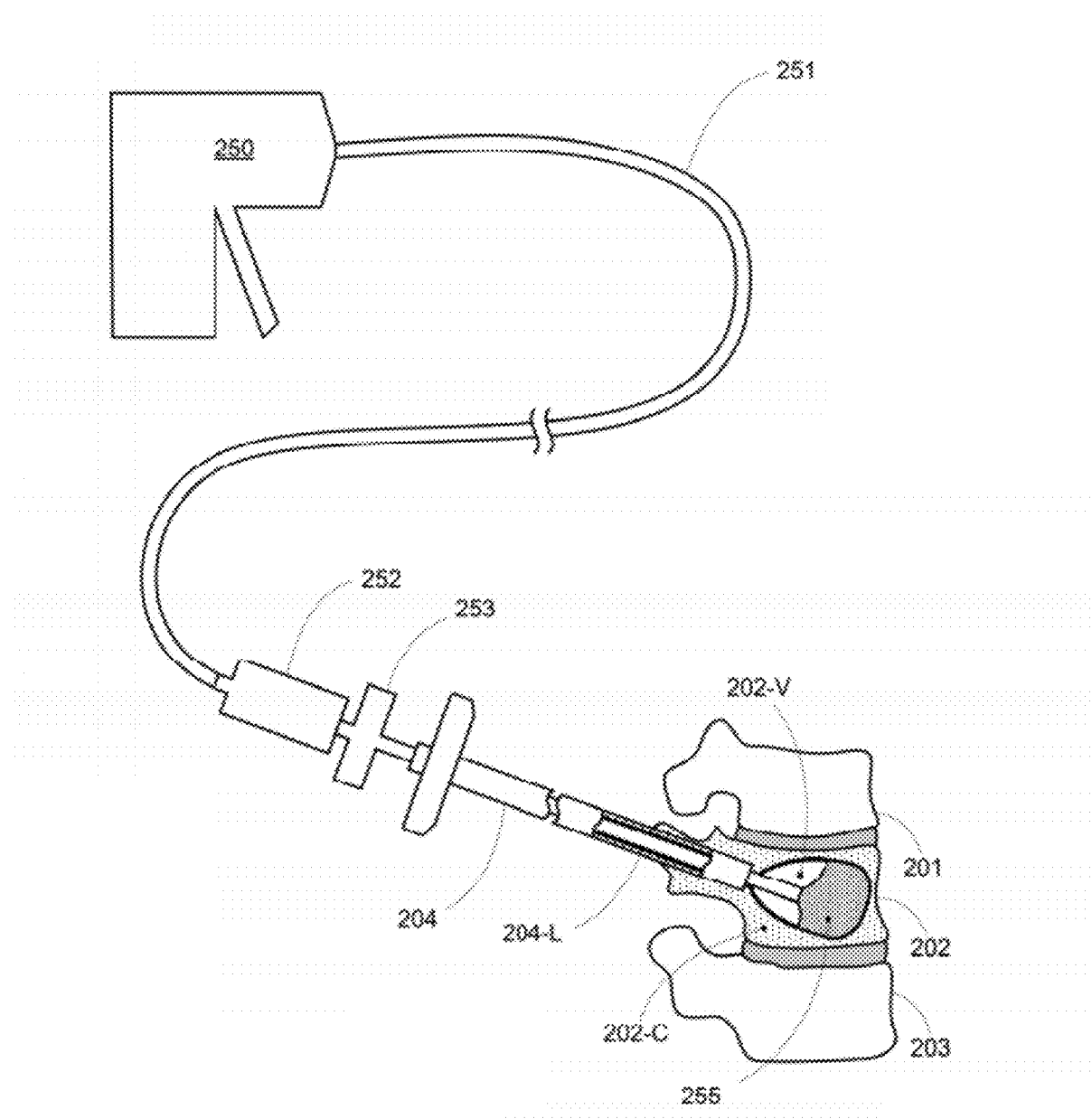

As shown in FIG. 2G, the result of the previously described expansion procedure is a well-defined cavity 202-V in cancellous bone 202-C, and a restoration of some or all of the original height of vertebra 202. Cavity 202-V can then be filled with bone filler material 255 (e.g., PMMA), as shown in FIG. 2G. A delivery nozzle 253 is inserted through cannula 204 and into cavity 202-V, and is used to direct bone filler material 255 into cavity 202-V.

As shown in FIG. 2G, in one embodiment, a quantity of bone filler material 255 can be housed in a cartridge 252 attached to delivery nozzle 253. A hydraulic actuator 250 can then be used to remotely express bone filler material 255 from cartridge 252 via a hydraulic line 251 (e.g., cartridge 252 can include a piston that is driven by the hydraulic pressure supplied by hydraulic line 251). Note, however, that in various other embodiments, bone filler material 255 can be delivered to cavity 202-V in any number of different ways (e.g., a high pressure cement delivery pump that delivers the cement to nozzle 253 through a flexible line, or a syringe or other delivery device filled with bone filler material 255 that is attached directly to nozzle 253), In addition, in various other embodiments, bone filler material 255 can be delivered in multiple portions of the same or different materials (e.g., a bone cement followed by a biologic agent).

Figure 2H:
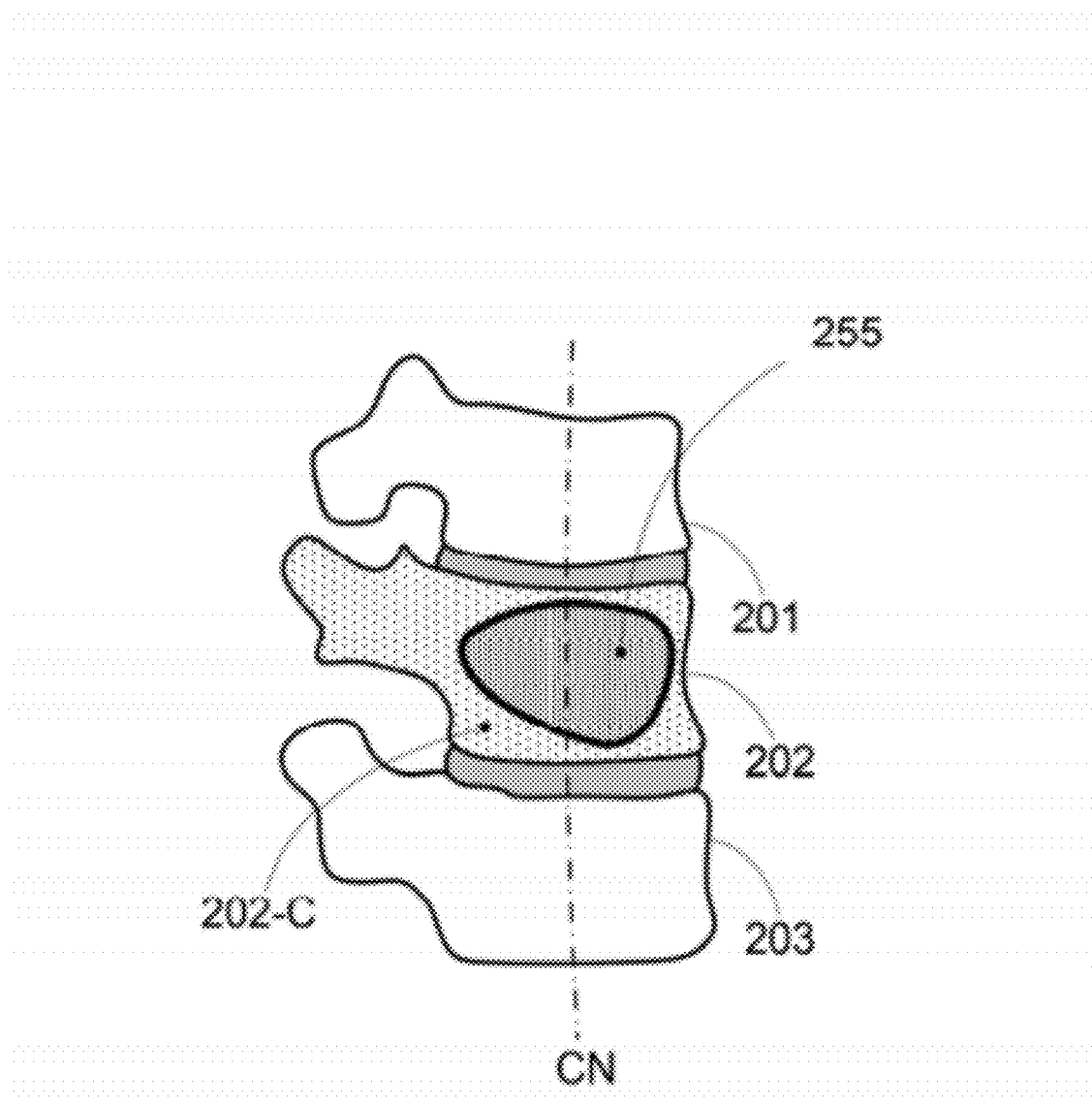

Once the filling operation is complete, delivery nozzle 253 and cannula 204 are removed from vertebra 202 (and the patient's body) as shown in FIG. 2H. Upon hardening, bone filler material 255 provides structural support for vertebra 202, thereby substantially restoring the structural integrity of the bone and the proper musculoskeletal alignment of the spine. As shown in FIG. 2H, due to the restoration of height in fractured vertebra 202, the abnormal curvature CK shown in FIG. 2A is corrected to a normal curvature CN. In this manner, the pain and attendant side effects of a vertebral compression fracture can be addressed by a minimally invasive kyphoplasty procedure.

As noted above, the beneficial vertebral height restoration capabilities of inflatable bone tamp 230 are greatly enhanced by the outwardly tapering expansion characteristic of inflatable structure 240. This expansion characteristic can be achieved through any number of design elements, including lobes of different size and/or elasticity in a balloon, elasticity variations in the balloon walls (e.g., via discrete features or internal wall thickness variations), and internal or external restraints.

Figure 3A:
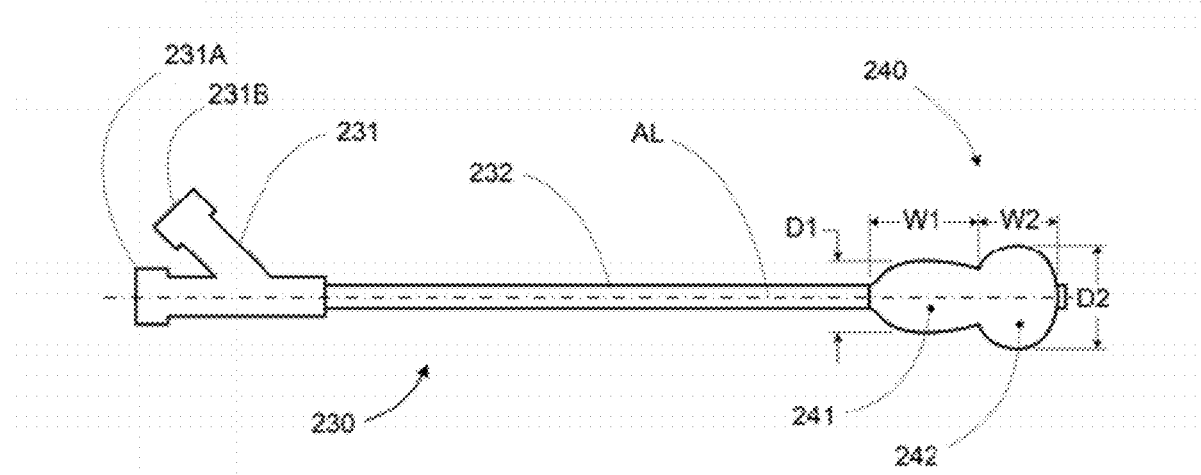
FIGS. 3A-3E show an inflatable bone tamp that includes a dual-lobed balloon that creates an outwardly tapering inflation profile.

For example, FIG. 3A shows an embodiment of inflatable bone tamp 230 that includes an inflatable structure 240 having a proximal lobe 241 and a distal lobe 242. Proximal lobe 241 has a maximum non-distended (i.e., non-stretched) radial diameter D1 (i.e., a maximum diameter perpendicular to a longitudinal axis AL), and distal lobe 242 has a maximum non-distended radial diameter D2, with diameter D2 being greater than diameter D1. As described in greater detail below, inflatable structure 240 can be formed from a compliant, or semi-compliant material (e.g., polyurethane) such that it continues to exhibit distally enlarging elastic expansion as it is inflated.

Figure 3B:
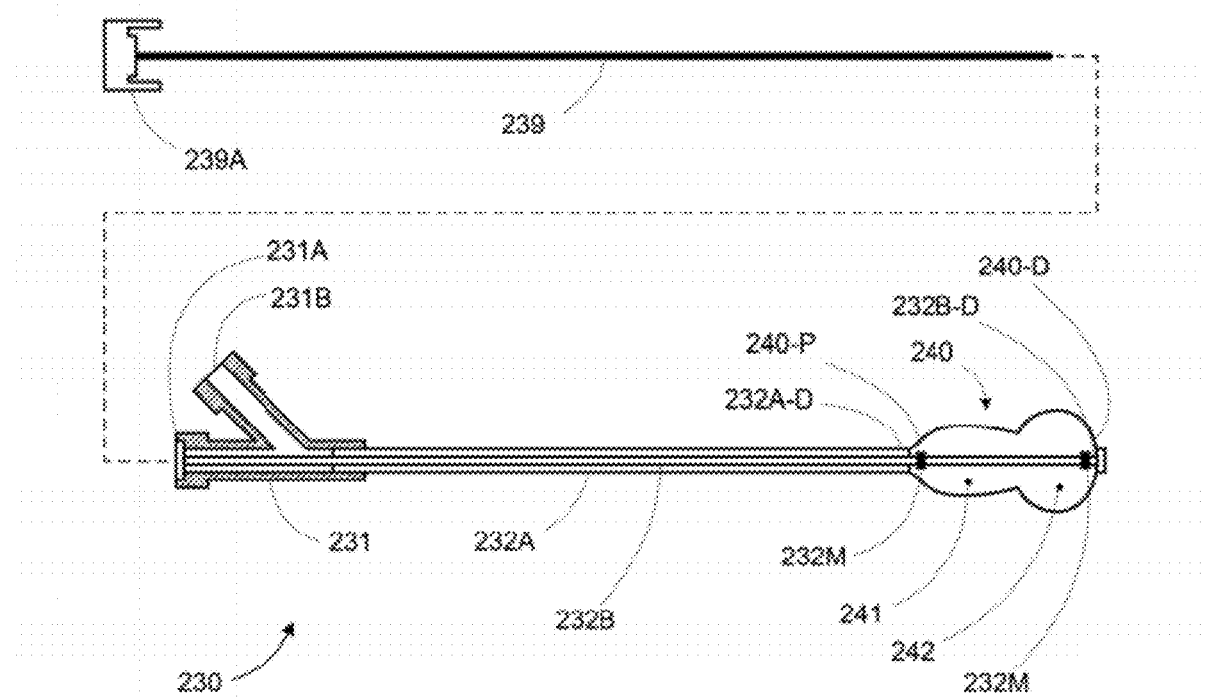

FIG. 3B shows an exemplary cross-sectional view of inflatable bone tamp 240 shown in FIG. 3A. Shaft 232 includes an outer catheter 232A coupled to a proximal end 240-P of expandable structure 240 (i.e., to proximal lobe 241) and an inner catheter 232B disposed within outer catheter 232A coupled to a distal end 240-D of inflatable structure 240 (i.e., to distal lobe 242). Inflatable structure 240 can therefore be inflated through a lumen formed between outer catheter 232A and inner catheter 242B (e.g., with inflation fluid input via a fitting 231B of connector 231).

In one embodiment, an optional stiffening stylet 239 can be removably inserted into the lumen of inner catheter 232B to provide some rigidity to inflatable structure 240 during placement, inflation, and/or removal of inflatable bone tamp 230 during a kyphoplasty procedure. In such an embodiment, the distal end of inner catheter 232B could be closed off to prevent unwanted material ingress into the lumen of inner catheter 232B. Note that in various other embodiments, shaft 232 can be a single catheter coupled, for example, to the proximal end 240-P of inflatable structure 240 (with distal end 240-D not being attached to shaft 232).

In another embodiment, radiopaque markers 232M can be placed at one or more locations on inflatable bone tamp 240 to assist in visualization of inflatable bone tamp 230 during the procedure. For example, as shown in FIG. 3B, markers 232M could be placed on inner catheter 232B adjacent to the proximal end 240-P and distal end 240-D of inflatable structure 240. Various other marker locations will be readily apparent.

Figure 3C:
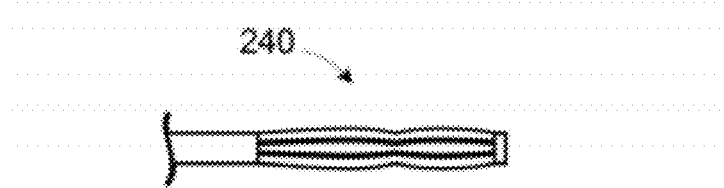
Figure 3D:
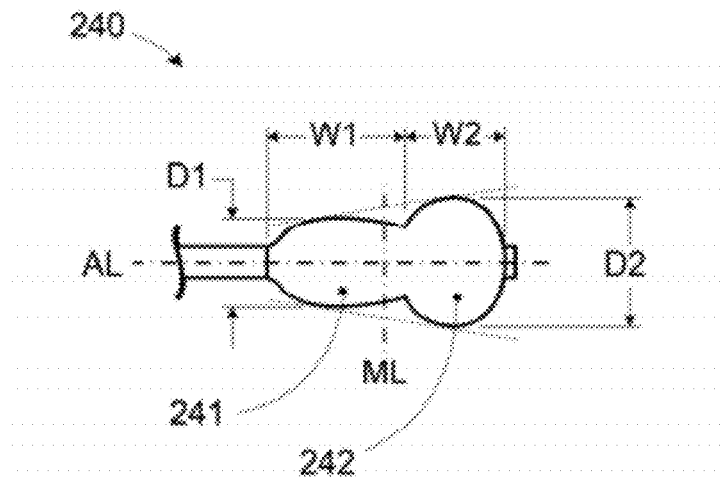
Figure 3E:
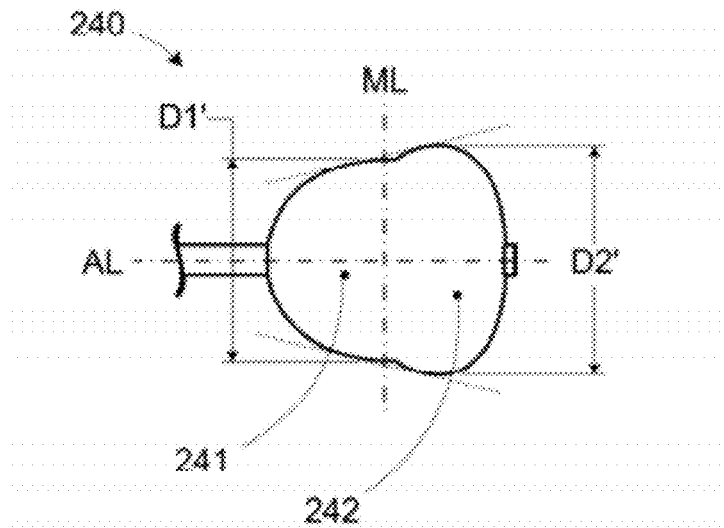

FIGS. 3C-3E depict an exemplary inflation sequence for a dual-lobed balloon 240 as described with respect to FIGS. 3A and 3B. In FIG. 3C, inflatable structure 240 is depicted in a fully deflated state, to enable insertion and removal of inflatable bone tamp 230 through cannula 204. FIG. 3D shows inflatable structure 240 in an inflated, non-distended configuration, in which the material of inflatable structure 240 has not yet begun to stretch. The maximum non-distended diameter D2 of distal lobe 242 is greater than the maximum non-distended diameter D1 of proximal lobe 241.

Note that FIG. 3D depicts the axial length W1 of proximal lobe 241 as being greater than the axial length W2 of distal lobe 242. This configuration can further enhance the distally enlarging characteristic of inflatable structure 240 by causing distal lobe 242 to expand (i.e., increase its diameter D2) more than the expansion of proximal lobe 241 (i.e., the increase in its diameter D1) for a given volume of inflation fluid delivery to inflatable structure 240. However, in various other embodiments, axial length W1 can be equal to or less than axial length W2.

Note that in various other embodiments, distal lobe 242 can be configured to have an elasticity greater than that of proximal lobe 241 (e.g., via different processing during the manufacturing process or through the use of different materials). In such constructions, maximum non-distended diameter D2 of distal lobe 242 need not necessarily be greater than maximum non-distended diameter D1 of proximal lobe 241, as the elasticity differential between the two lobes can enable the desired outwardly tapering expansion profile.

FIG. 3E shows inflatable structure 240 in an inflated, distended state, in which the inflation pressure within inflatable structure 240 has elastically deformed (stretched) the material forming lobes 241 and 242 outward. In this manner, inflatable structure 240 maintains an outward taper as it expands into its inflated, distended configuration. Note that as used herein, "outwardly tapering expansion profile" describes a generally increasing diameter or major dimension (e.g., height) in a distal direction. Furthermore, as shown in FIGS. 3D and 3E, an outward taper need not necessarily be a continually increasing diameter/major dimension, but rather refers to a state in which a maximum diameter D2 (or D2') of the distal half of inflatable structure 240 (i.e., distal of a midline ML) is greater than a maximum diameter D1' of the proximal half (i.e., proximal of the midline CL).

Figures 4A, 4B:
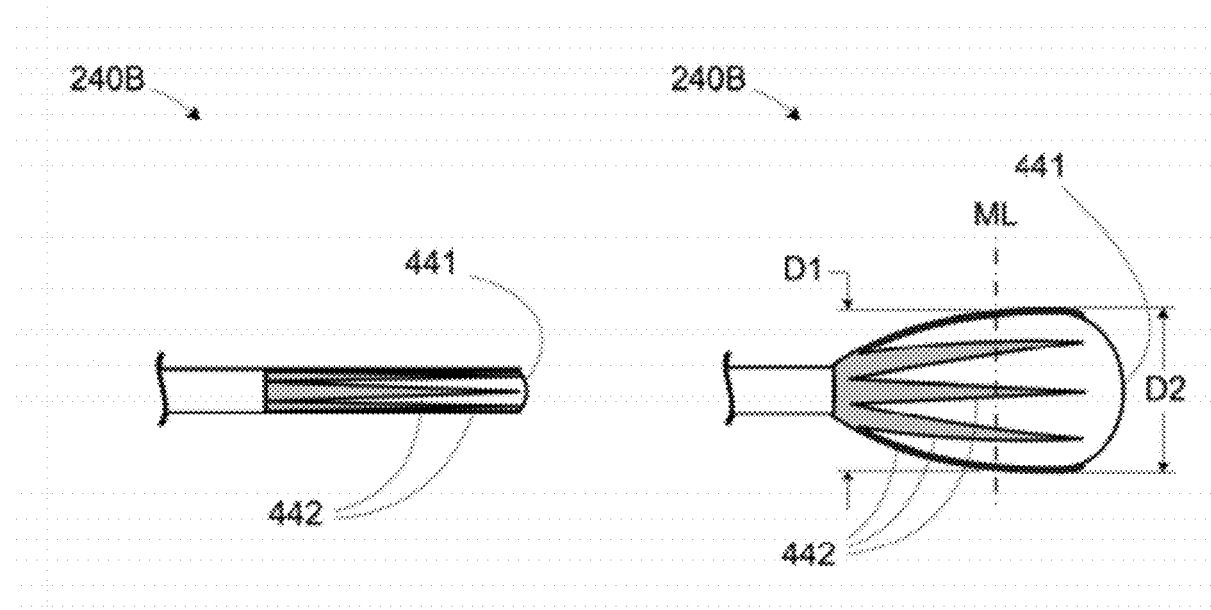
Figure 4C:
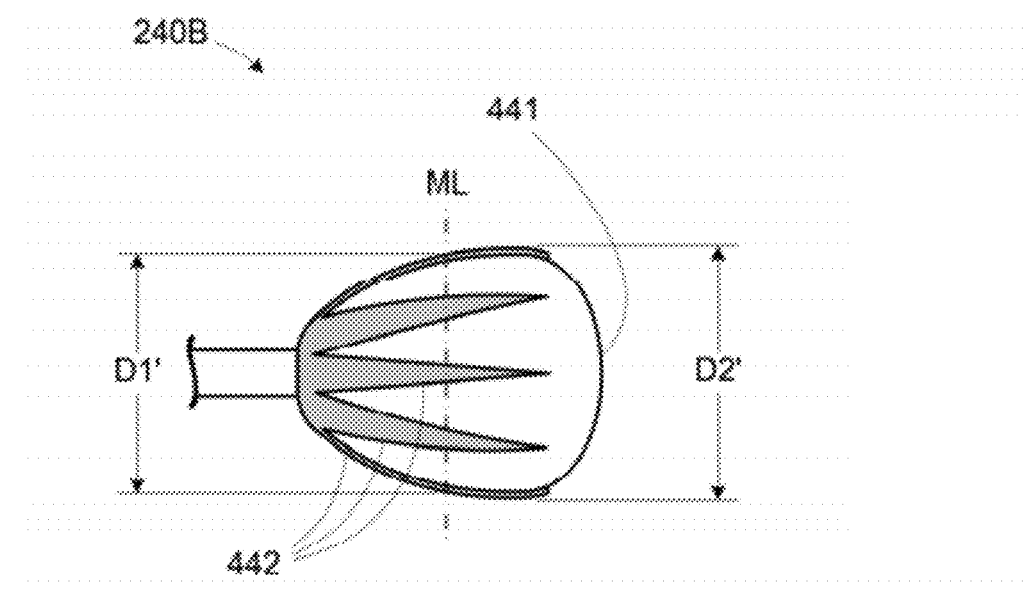

Note that while a dual-lobed balloon is depicted and described in FIGS. 3A-3E for exemplary purposes, in various other embodiments, outwardly tapering inflatable structure 240B can be formed using any construction. For example, FIGS. 4A-4C show an embodiment of outwardly tapering inflatable structure 240B that includes constraining features 442 disposed at various regions along an inflatable element 441. Constraining features 442 include a series of ribs or strips that taper towards the distal end of inflatable element 441. As described in greater detail below, the wall thickness variations created by constraining features 442 cause inflatable structure 240B to exhibit an outwardly tapering expansion profile.

FIG. 4A shows inflatable structure 240B fully deflated for transport though a cannula. FIG. 4B shows inflatable structure 240B in an inflated, non-distended configuration, defined primarily by the configuration of inflatable element 441. Inflatable element 441 incorporates an integral outward taper, such that the maximum distal dimension D2 of inflatable structure 240B is greater than its maximum proximal dimension D1. The pattern of constraining features 442 can also be seen in FIG. 4B, although the physical effect of those features is minimal while inflatable structure 240B is in a non-distended state.

FIG. 4C shows inflatable structure 240B in an inflated, distended configuration, The additional wall thickness towards the proximal end of inflatable element 441 provided by constraining features 442 causes inflatable structure 240B to expand more distally than proximally, thereby maintaining an outwardly tapering profile (i.e., maximum distal dimension D2' is greater than maximum proximal dimension D1'). Note that in various other embodiments, constraining features 442 can take any shape and arrangement that results in an outwardly tapering expansion profile for inflatable structure 240B (i.e., any wall thickness variations in inflatable element 441 that allow for greater distal than proximal expansion).

In various other embodiments, inflatable structure 240 can include internal features that constrain proximal expansion more than distal expansion. For example, FIGS. 4D and 4E show the inflated, non-distended configuration, and the inflated, distended configuration, respectively of an inflatable structure 240C that includes an internal web 443 connected within inflatable element 441. Internal web 443 constrains the proximal expansion of inflatable element 441 such that the maximum distal dimensions D2 (non-distended) and D2' (distended) are greater than the maximum proximal dimensions D1 (non-distended) and D1' (distended), respectively. Internal web 443 can be configured in any manner that creates this expansion profile (e.g., a web having a wall thickness that is greater proximally than distally). Note that while depicted as a single web for explanatory purposes, in various other embodiments, internal web 443 can include any number of elements in any arrangement configured to provide the desired expansion profile for inflatable structure 240C.

In various other embodiments, inflatable structure 240 can include one or more external restraints such as shown in FIGS. 4F and 4G. Inflatable structure 240D includes an inflatable element 441 over which is disposed an external restraint 444. Although depicted as a single sleeve-like structure for exemplary purposes, in various other embodiments external restraint 444 can be formed from multiple pieces, as indicated by the dotted lines (e.g., multiple rings, strings, or straps, among others), or can be a stent or scaffold-like structure.

As shown in FIGS. 4F and 4G, external restraint 444 constrains expansion of the proximal portion of inflatable element 441 such that inflatable structure 240D exhibits maximum distal dimensions D2 (non-distended) and D2' (distended) that are greater than the maximum proximal dimensions D1 (non-distended) and D1' (distended), respectively. Note that although external restraint 441 is depicted as being substantially inelastic for exemplary purposes, in various other embodiments, external restraint 441 can be formed from elastic material that simply limits the expansion of the proximal end of expandable element 441 relative to the expansion of its distal end.

Note further that in various other embodiments, an outwardly tapering inflatable structure may exhibit its outwardly tapering characteristic only after distended expansion begins. For example, in one embodiment, inflatable element 441 of FIGS. 4F and 4G could have an inflated, non-distended shape that is substantially symmetrical (or even inwardly tapering) about midline ML (i.e., maximum distal dimension D2 is less than or equal to maximum proximal dimension D1). However, inflation beyond that non-distended maximum proximal dimension D1 could be prevented by external restraint 443, thereby allowing the distal portion of inflatable element 441 to become larger to effect the desired outward taper in its inflated, distended configuration. Various other embodiments will be readily apparent.

Figure 5:
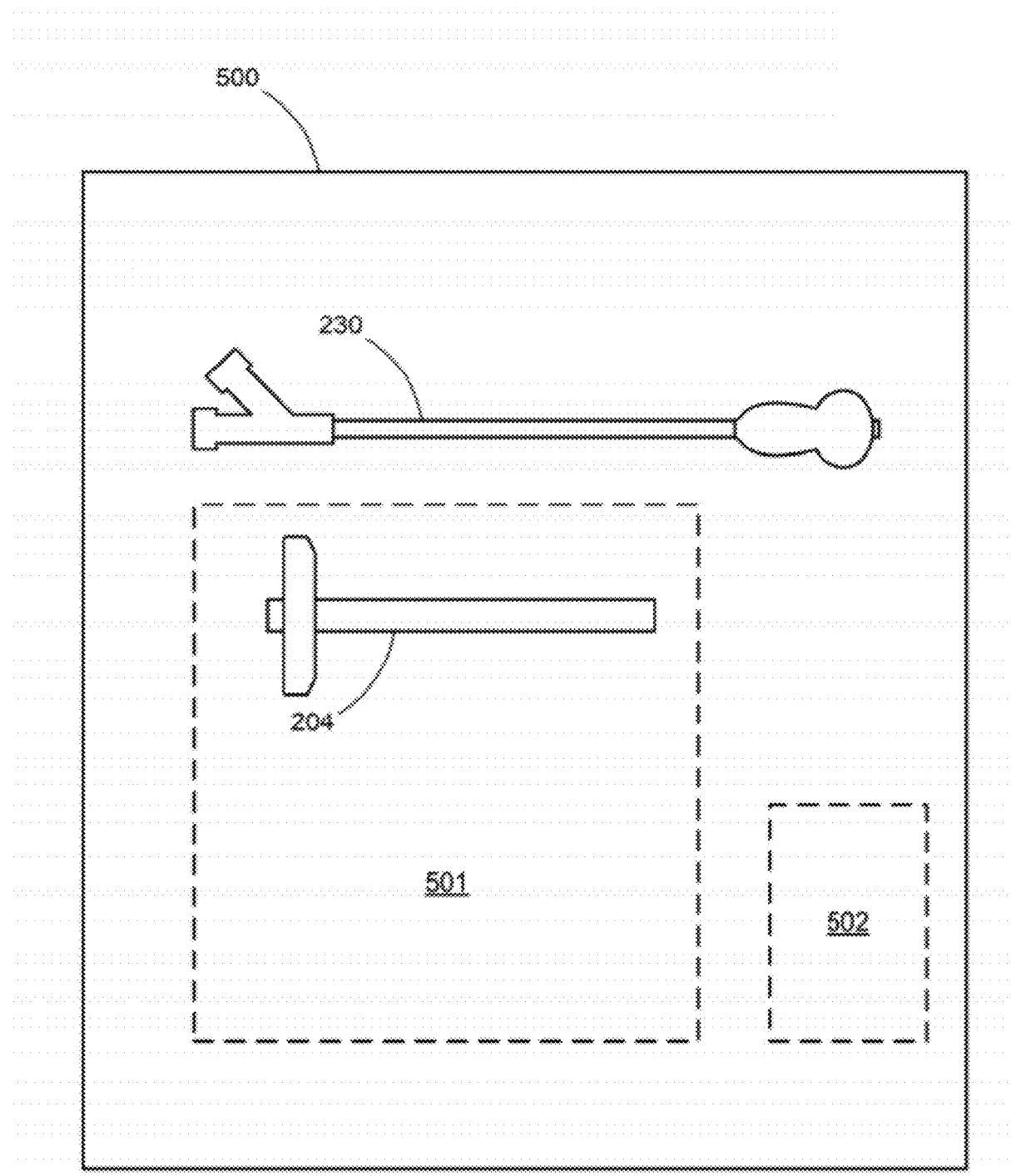
FIG. 5 shows a kit that includes an inflatable bone tamp that exhibits an outwardly tapering inflation profile.

FIG. 5 shows a diagram of a kit 500 for use in performing a surgical procedure, such as a kyphoplasty procedure described with respect to FIGS. 2A-2H above. Kit 500 includes an inflatable bone tamp 230 (e.g., as described above with respect to FIGS. 3A-3E and 4A-4G) having an outwardly tapering expansion profile. In various embodiments, kit 500 can further include optional additional instruments 501, such as a cannula 204 sized to receive inflatable bone tamp 230, an introducer, guide pin, drill, curette, and/or access needle, among others (only cannula 204 is shown for clarity). In various other embodiments, kit 500 can further include optional directions for use 502 that provide instructions for using inflatable bone tamp and optional additional instruments 501 (e.g., instructions for performing a kyphoplasty procedure using inflatable bone tamp 230 and optional additional instruments 501).

Figure 6:
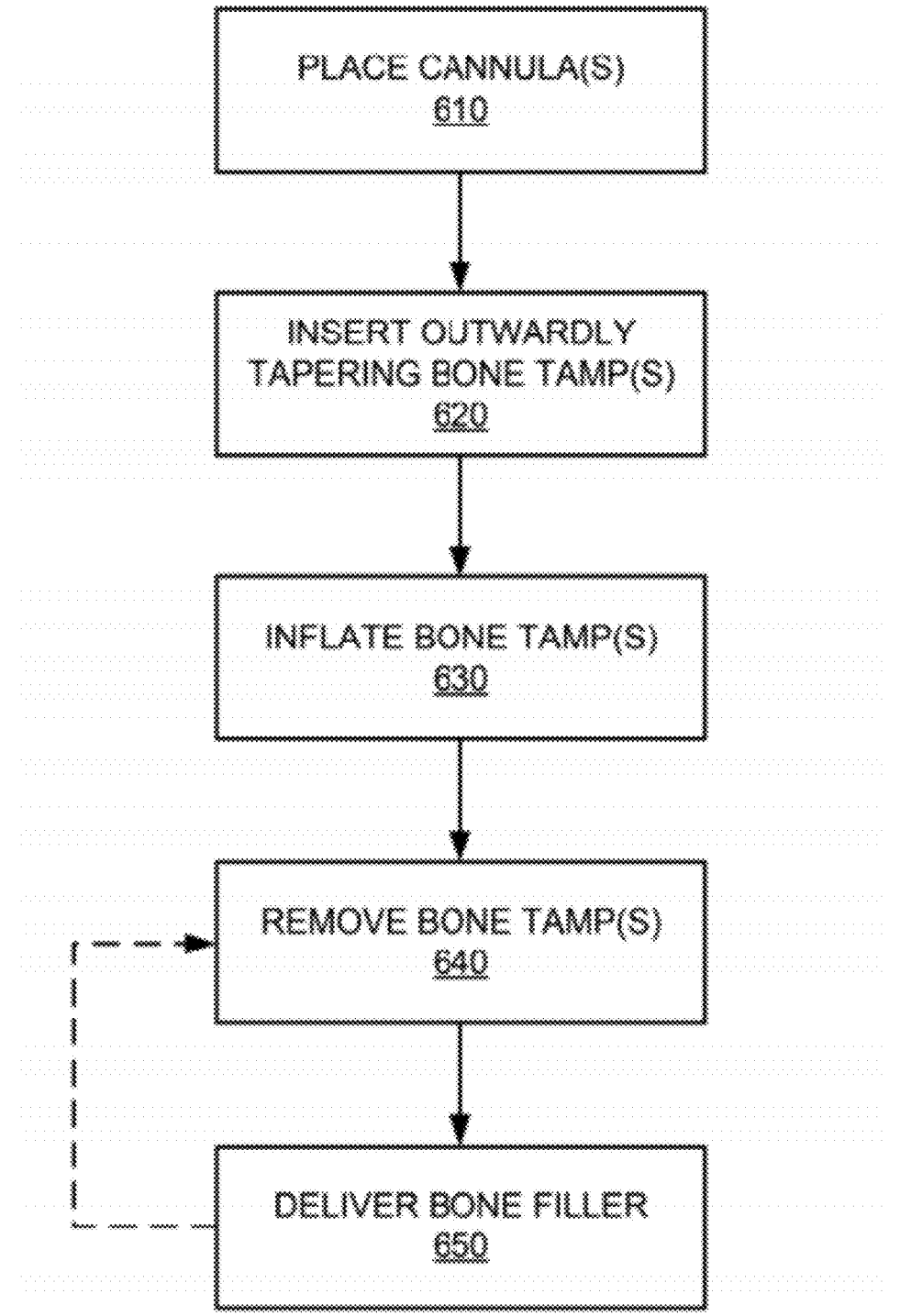
FIG. 6 shows a flow diagram for a surgical procedure that makes use of an inflatable bone tamp(s) that exhibit an outwardly tapering inflation profile(s).

FIG. 6 shows a flow diagram of a process for performing a surgical procedure such as kyphoplasty using an inflatable bone tamp exhibiting an outwardly tapering inflation profile. In a PLACE CANNULA(S) step 610, a cannula is positioned within a patient to provide a path to a target surgical location (e.g., as described with respect to FIG. 2B). Note that although a unilateral procedure is described above for clarity, in various other embodiments, a bilateral procedure can be used (e.g., placing two cannulas to provide access through both pedicles of a vertebra).

Then, in an INSERT OUTWARDLY TAPERING BONE TAMP(S) step 620, an inflatable bone tamp exhibiting an outwardly tapering inflation profile (e.g., as described with respect to FIGS. 3A-3E and 4A-4G) is placed within the patient through the cannula (e.g., as described with respect to FIG. 2C). Note once again that if multiple cannulas have been placed in step 610, an inflatable bone tamp can be inserted into each cannula (with at least one of the inflatable bone tamps exhibiting an outwardly tapering inflation profile).

Next, in an INFLATE BONE TAMP(S) step 630, the inflatable bone tamp(s) is (are) inflated to create a cavity in cancellous bone and, ideally, at least partially restore the original cortical bone profile (e.g., as described with respect to FIGS. 2C and 2D). As described above, the outwardly tapering inflation provide of the inflatable bone tamp increases the likelihood that this desirable cortical bone manipulation (e.g., height restoration in a vertebral compression fracture). Note that if multiple inflatable bone tamps have been introduced in step 620, their inflation can be sequential, simultaneous, sequentially incremental (e.g., partially inflating one before partially or fully inflating another), or any other order.

The inflatable bone tamp is then deflated and withdrawn from the patient in a REMOVE BONE TAMP step 640 (e.g., as described with respect to FIG. 2F), and in a DELIVER BONE FILLER step 650, a bone filler material (e.g., bone cement) is conveyed to the cavity formed by the inflatable bone tamp to create a permanent reinforcing structure within the bone (e.g., as described with respect to FIGS. 2G and 2H).

Note that if multiple inflatable bone tamps have been placed within the patient (e.g., in a bilateral procedure) in step 620, one or more of those inflatable bone tamps can be left (inflated) within the patient to provide support for the bone structure during subsequent material delivery during step 650. The process can then loop back to step 640 and then step 650 until all inflatable bone tamps have been removed, and all the resulting cavities in the bone have been filled with bone filler material.

While various embodiments of the invention have been described above, it should be understood that they have been presented by way of example only, and not limitation. Where methods and steps described above indicate certain events occurring in certain order, those of ordinary skill in the art having the benefit of this disclosure would recognize that the ordering of certain steps may be modified and that such modifications are in accordance with the variations of the invention. Additionally, certain steps may be performed concurrently in a parallel process when possible, as well as performed sequentially as described above. Thus, the breadth and scope of the invention should not be limited by any of the above-described embodiments, but should be defined only in accordance with the following claims and their equivalents. While the invention has been particularly shown and described with reference to specific embodiments thereof, it will be understood that various changes in form and details may be made.

The invention claimed is:

1. A device for performing a surgical procedure, the device comprising:
an elongate element having a distal end; and
an inflatable structure coupled to the distal end of the elongate element,
wherein the inflatable structure comprises:
a first lobe, a proximal end of the first lobe being contiguous with the distal end of the elongate element; and
a second lobe, a proximal end of the second lobe being contiguous with a distal end of the first lobe;
a neck region defined at a junction between the first lobe and the second lobe, wherein a maximum wall thickness of the neck region is greater than a minimum wall thickness of the first lobe, and wherein the maximum wall thickness of the neck region is greater than the minimum wall thickness of the second lobe, wherein when in an inflated, non-distended condition, a maximum radial diameter of the second lobe is greater than a maximum radial diameter of the first lobe, wherein an axial length of the first lobe is greater than an axial length of the second lobe.

2. The device of claim 1, wherein a first distance between the proximal end of the first lobe and the distal end of the first lobe is greater than a second distance between the proximal end of the second lobe and a distal end of the second lobe.

3. The device of claim 1, wherein the elongate element comprises: an outer shaft defining a first internal lumen; and an inner shaft disposed within the first internal lumen, wherein the proximal end of the first lobe is connected to a distal end of the outer shaft, wherein a distal end of the second lobe is connected to a distal end of the inner shaft.

4. The device of claim 3, wherein the inner shaft defines a second internal lumen, the device further comprising a stylet removably disposed within the second internal lumen, the stylet being sized to extend to at least the distal end of the second lobe.

5. A system for performing a surgical procedure, the system comprising: a cannula defining an access lumen; and an inflatable bone tamp sized to fit within the access lumen, the inflatable bone tamp comprising: an elongate element having a distal end; and an inflatable structure coupled to the distal end of the elongate element, wherein the inflatable structure comprises:
- a first lobe, a proximal end of the first lobe being contiguous with the distal end of the elongate element; and
- a second lobe, a proximal end of the second lobe being contiguous with a distal end of the first lobe;
- a neck region defined at a junction between the first lobe and the second lobe, wherein a maximum wall thickness of the neck region is greater than a minimum wall thickness of the first lobe, and wherein the maximum wall thickness of the neck region is greater than the minimum wall thickness of the second lobe;
- wherein when in an inflated, non-distended condition, a maximum radial diameter of the second lobe is greater than a maximum radial diameter of the first lobe;
- wherein an axial length of the first lobe is greater than an axial length of the second lobe.

6. The system of claim 5, wherein a first distance between the proximal end of the first lobe and the distal end of the first lobe is greater than a second distance between the proximal end of the second lobe and a distal end of the second lobe.

7. The system of claim 5, wherein the elongate element comprises: an outer shaft defining a first internal lumen; and an inner shaft disposed within the first internal lumen, wherein the proximal end of the first lobe is connected to a distal end of the outer shaft, wherein a distal end of the second lobe is connected to a distal end of the inner shaft.

8. The system of claim 7, wherein the inner shaft defines a second internal lumen, the device further comprising a stylet removably disposed within the second internal lumen, the stylet being sized to extend to at least the distal end of the second lobe.

* * * * *